(12) United States Patent
Bach et al.

(10) Patent No.: US 8,444,940 B2
(45) Date of Patent: May 21, 2013

(54) REACTOR FOR PRODUCING $C_2$- TO $C_8$-OLEFINS FROM A MATERIAL FLOW CONTAINING OXYGENATE, WATER VAPOR AND ONE OR MORE HYDROCARBONS

(75) Inventors: Hermann Bach, Heiligenroth (DE); Lothar Brehm, Niederdorfelden (DE); Jurgen Bohle, Frankfurt am Main (DE); Gunter Quass, Frankfurt am Main (DE); Gunther Heinz, Selters-Eisenbach (DE); Katja Bartels, Frankfurt am Main (DE); Heinrich Dörr, Rimbach (DE); Harald Kömpel, Neu-Isenburg (DE)

(73) Assignee: Lurgi GmbH, Frankfurt am Main (DE)

( * ) Notice: Subject to any disclaimer, the term of this patent is extended or adjusted under 35 U.S.C. 154(b) by 801 days.

(21) Appl. No.: 12/303,227

(22) PCT Filed: Apr. 21, 2007

(86) PCT No.: PCT/EP2007/003512
§ 371 (c)(1),
(2), (4) Date: Jul. 6, 2009

(87) PCT Pub. No.: WO2007/140844
PCT Pub. Date: Dec. 13, 2007

(65) Prior Publication Data
US 2010/0063337 A1   Mar. 11, 2010

(30) Foreign Application Priority Data
Jun. 3, 2006   (DE) .......................... 10 2006 026 103

(51) Int. Cl.
*B01J 8/02* (2006.01)
(52) U.S. Cl.
USPC ........... 422/618; 422/621; 422/631; 422/635; 422/638; 422/646; 422/640

(58) Field of Classification Search
USPC ................. 422/600, 606, 618, 621, 631, 635, 422/638, 646; 585/640, 638
See application file for complete search history.

(56) References Cited

U.S. PATENT DOCUMENTS 2,306,011 A * 12/1942 Burk et al. ..................... 422/632
3,746,515 A    7/1973 Friedman
(Continued)

FOREIGN PATENT DOCUMENTS

DE    1258003 B    1/1968
DE    10233975 A1    2/2004
(Continued)

OTHER PUBLICATIONS

English language abstract for DE 10233975 which published Feb. 12, 2004.

*Primary Examiner* — Nina Bhat
(74) *Attorney, Agent, or Firm* — Norris McLaughlin & Marcus PA

(57) ABSTRACT

A reactor is described for the production of $C_2$ to $C_8$ olefins from gaseous oxygenate and $H_2O$ and one or more material flows containing $C_2$ $C_4$, $C_5$, $C_6$, $C_7$, $C_8$ olefin and paraffin at 400° to 470° C., wherein several reaction stages which the material flow can pass through from the top to the bottom, each consisting of a support base with a catalyst layer situated on it, are arranged in a closed, upright container. In order to be able in each case to lower the temperature of the reaction mixture leaving the reaction stages before it enters into the next reaction stage, it is provided that each support base consists of cells which are placed closely next to each other with no gaps and which are securely attached to each other and filled with catalyst, and in the space formed by two neighboring reaction stages, respectively, an assembly of nozzle tubes is installed for spraying a liquid phase containing $H_2O$ and DME and/or MEOH, using a water-saturated gas phase containing mainly DME and/or MEOH, in the direction of the following reaction stage downstream.

19 Claims, 3 Drawing Sheets

U.S. PATENT DOCUMENTS

| | | |
|---|---|---|
| 3,824,081 A | 7/1974 | Smith |
| 4,542,252 A | 9/1985 | Graziani |
| 4,544,781 A | 10/1985 | Chao |
| 5,084,247 A * | 1/1992 | Heisel et al. .................. 422/200 |
| 7,033,553 B2 * | 4/2006 | Johnston et al. ............. 422/199 |
| 7,338,645 B2 * | 3/2008 | Jones et al. ................... 422/240 |
| 7,465,845 B2 * | 12/2008 | Xu et al. ........................ 585/640 |
| 8,124,035 B2 * | 2/2012 | Riley ............................. 422/630 |
| 2006/0063956 A1 | 3/2006 | Kalnes |

FOREIGN PATENT DOCUMENTS

| | | |
|---|---|---|
| EP | 0088494 A1 | 9/1983 |
| WO | 03/086607 A | 10/2006 |

\* cited by examiner

REACTOR FOR PRODUCING C$_2$- TO C$_8$-OLEFINS FROM A MATERIAL FLOW CONTAINING OXYGENATE, WATER VAPOR AND ONE OR MORE HYDROCARBONS

This application is a 371 application of PCT/EP2007/003512 filed Apr. 21, 2007, which claims priority to the German application DE 10 2006 026 103.8 filed Jun. 3, 2006.

The invention relates to a reactor for producing C$_2$- to C$_8$-olefins, preferably propylene, from gaseous oxygenate, preferably dimethylether (DME) and/or methanol (MeOH) as well as H$_2$O and a material flow containing one or more of the hydrocarbons C$_2$-, C$_4$-, C$_5$-, C$_6$-, C$_7$-, C$_8$-olefins and -paraffins having a temperature of 400 to 470° C., comprising several reaction stages arranged within an enclosed, vertical vessel through which the material flow flows from top to bottom, each of such stages being composed of a tray carrying a fixed-bed zone formed by a packing of granular molecular-sieve catalyst. The invention also relates to a method of operating the reactor.

A device for producing propylene from MeOH is known from DE-A-102 33 975. In that device, a gaseous feed stream composed of MeOH/DME and water at operating temperatures of 250 to 460° C. is routed through several reaction stages arranged in a vertical vessel, one on top of the other, through which the feed stream flows from top to bottom. Each reaction stage is composed of a support, a grate resting on it featuring a mesh width of ¼" and a 300-mm thick layer of SiO$_2$ or Al$_2$O$_3$ balls arranged above it on which a 750-mm thick layer of shape-selective catalyst of the Pentasil type made up of cylindrical particles with a diameter of 1/16" and a length of ⅛" is accommodated, covered by a 200-mm thick layer of ceramic balls having a diameter of ½" on top of which wire mesh is placed. In the reaction stages the feed stream entering at inlet temperatures of 400 to 460° C. is converted at pressures ranging from 0.5 to 3.0 bar. To cool the reaction mixture leaving the reaction stages, heat exchangers are arranged between the reaction stages by means of which the reaction mixture is cooled in each case to a temperature of 400 to <460° C. The cross section of the inlet openings of the heat exchangers corresponds in each case to the cross section of the outlet openings of the preceding reaction stage. The product stream discharged from the vessel is split into a liquid phase containing DME, H$_2$O and MeOH as well as a gas phase containing hydrocarbons from which propylene is separated. This method has a disadvantage in that the reaction taking place in the reaction stages is not isothermal and cooling of the reaction mixture by means of the heat exchangers arranged between the reaction stages requires a comparatively elaborate design and takes place under unfavourable fluidic conditions.

It is an object of the invention to improve the initially described reactor and to provide a method for controlling the process for operating the reactor such that the temperature of the reaction mixture leaving the individual reaction stages, which is in the area of 400 to 500° C. as a result of the exothermal course of reaction, is first lowered to a temperature of 380 to 470° C. before the reaction mixture enters the next downstream reaction stage. Moreover, the introduction of the catalyst layer to the individual reaction stages is to be simplified and the flow through the catalyst layer rendered more efficient.

According to the present invention each tray is built up from cells arranged side by side without interspace and firmly connected with each other, and suspended freely inside the vessel, the cells being filled with a layer of molecular-sieve catalyst, and by providing, in the direction towards the next following downstream reaction stage, an atomizer system composed of an assembly of nozzle tubes, the interspace of which is in each case delimited above and below by two adjacent reaction stages, designed to evenly spray a liquid phase containing DME and/or MeOH, mainly consisting of H$_2$O at a temperature of 25 to 150° C. by means of a water-saturated gas phase mainly containing DME and/or MeOH and having a temperature of 170 to 300° C. By atomizing the liquid phase, the temperature of the reaction mixture leaving the reaction stage at a temperature of 400 to 500° C. is reduced to a level of 380 to 470° C. so that the course of reaction is quasi isothermal. The liquid phase may contain up to 30% (vol.) DME and/or MeOH and the gas phase up to 80% (vol.) DME and up to 30% (vol.) MeOH.

The molecular-sieve catalysts used are preferably synthetic zeolites of various types, for example ZSM-5, Pentasil, MFI-Z or MeAPSO.

The particles of the molecular-sieve catalyst are preferably cylindrical and feature a mean length of 3.5 to 7.0 mm or 2.1 to 4.5 mm and a mean diameter of 3.1 to 3.4 mm or 3.3 to 3.7 mm.

In a special embodiment of the invention, the layer thickness of the molecular-sieve catalyst filled into the cells of the tray is 100 to 1000 mm, increasing gradually downstream from one reaction stage to the next following, with the layer thickness of the first reaction stage being conveniently 100 to 500 mm and that of the last reaction stage, 500 to 1000 mm. Through this measure and by adapting the material flow rates, a constant residence time of the reaction mixture as required for the exothermal conversion, is ensured in all reaction stages.

The tray built up from numerous cells, preferably in the shape of cuboids, cubes or straight equilateral prisms exhibits sufficient bending rigidity to withstand the total weight composed of the dead weight, the weight of the molecular-sieve catalyst layer and the weight of the inert balls. The deflection of the tray is negligible, and free suspension of the tray in the vessel is ensured.

To prevent the molecular-sieve catalyst and the 100 to 400 mm thick layer of inert balls below it from falling out of the cells, the tray bottom is covered with wire mesh, expanded metal, perforated plate or similar. The inert balls have diameters ranging from 10 to 15 mm in the lower layer part and of 5 to 8 mm in the upper part. This kind of layer arrangement will prevent the formation of flow tunnels through which the reaction mixture might prematurely leak out of the reaction stage.

On the top face, the tray is likewise covered with mire mesh, expanded metal, perforated plate or similar on top of which a 50 to 200 mm thick layer of inert balls of 5 to 15 mm in diameter is placed. The provision of this layer ensures that the liquid phase sprayed in the interspace formed in each case by two adjacent reaction stages is safely and completely evaporated.

According to a special embodiment of the invention, the atomizer system is in each case composed of an assembly of nozzle tubes with twin-fluid nozzles arranged at regular intervals with external mixing effect, preferably with solid-cone characteristic at a jet angle of 15 to 35°. As a result of the external mixing effect of the gas and liquid phases, the throughput of the liquid phase which is mainly composed of H$_2$O and DME and/or MeOH and has a temperature of 25 to 150° C., and of the water-saturated gas phase which is mainly composed of DME and MeOH and has a temperature of 170 to 300° C., can be adjusted independently of each other.

In an embodiment of the invention, the atomizer system installed in each case between two adjacent reaction stages consists of mirror-image arranged nozzle tubes closed at the end pointing in the direction of flow and introduced horizontally from the vessel periphery on both sides of a vertical plane enclosing the vessel axis and laid parallel to each other at regular spacing in each case perpendicularly to the vertical plane enclosing the vessel axis, where the distance between the nozzle tube ends and the plane enclosing the vessel axis is between 20 and 500 mm. This arrangement ensures that the free path of the liquid is constrained.

An optimal cooling effect can be achieved by means of the atomized liquid phase when in the case of cells of cube or cuboid design forming the tray the nozzle tube has in each case the same straight-line distance from the double or single cell wall and is arranged in the vertical plane enclosing this cell wall.

In special cases it is possible to design the nozzle tubes in the form of involutes.

To operate the reactor, gaseous oxygenate, preferably DME and/or MeOH as well as a process stream containing $H_2O$ and having a temperature of 150 to 300° C. is cooled to a temperature of 100 to 160° C., separated into a liquid phase and a gas phase with the liquid and the gas phases being split into several partial streams, the number of which corresponds in each case to the number of interspaces between the reaction stages. Referred to one interspace, in each case one gas phase partial stream is routed to an atomizer after being heated to a temperature of 170 to 300° C. and a liquid phase partial stream, after cooling to a temperature of 25 to 150° C., are sprayed into the interspace. These measures make it possible to adjust the inlet temperature of the reaction mixture leaving the reaction stage into the interspace to the desired level before it enters the next following reaction stage.

In order to achieve total evaporation of the liquid phase, it is advisable to atomize the liquid phase by means of the gas phase into a fine droplet spectrum at a diameter of 10 and 100 μm.

BRIEF DESCRIPTION OF THE DRAWINGS

The invention is explained in detail below on the basis of an embodiment example and of drawings.

The figures illustrate the following details.

Figure 1:
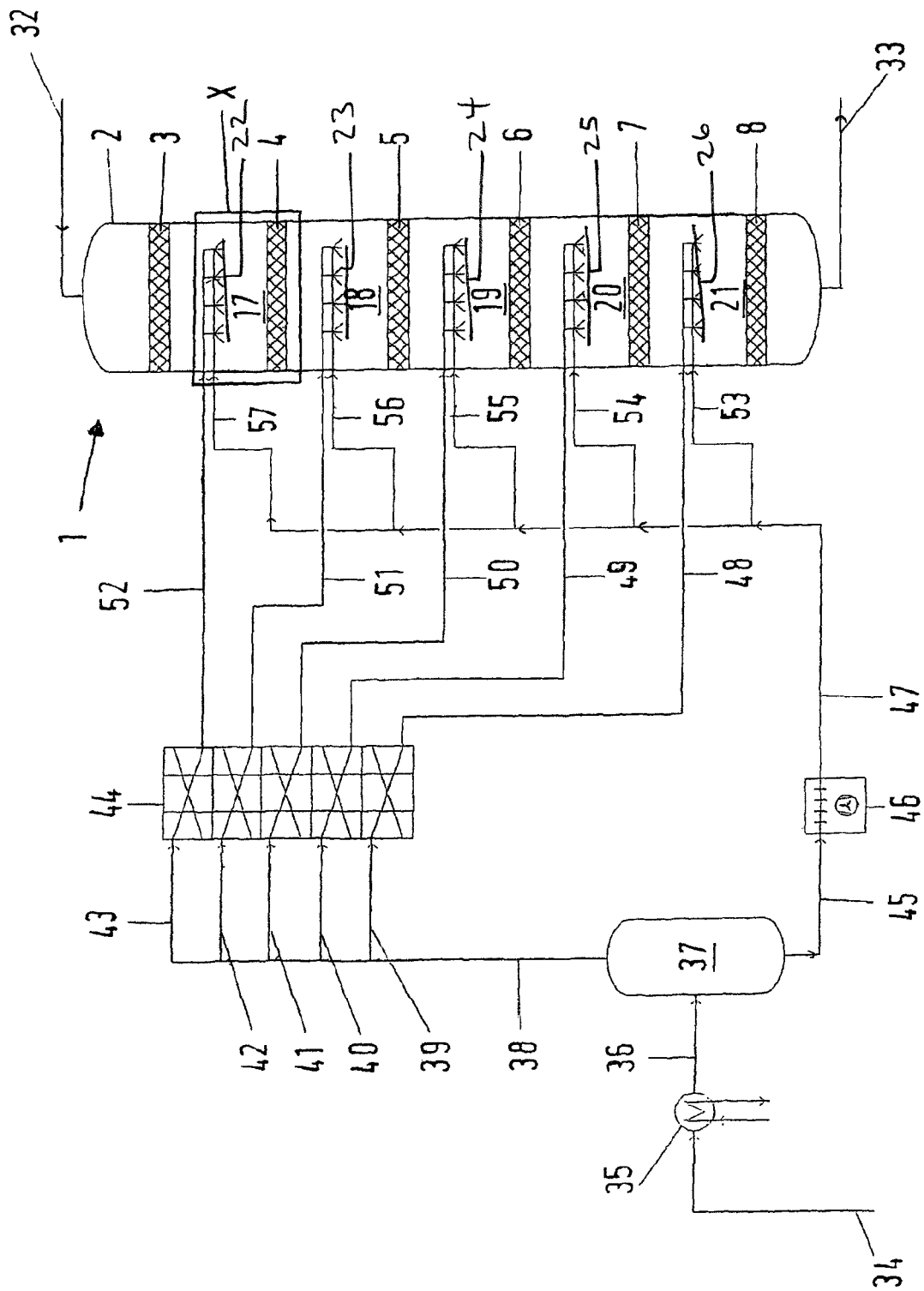
FIG. 1 a process flow diagram with a schematically drawn reactor
Figure 2:
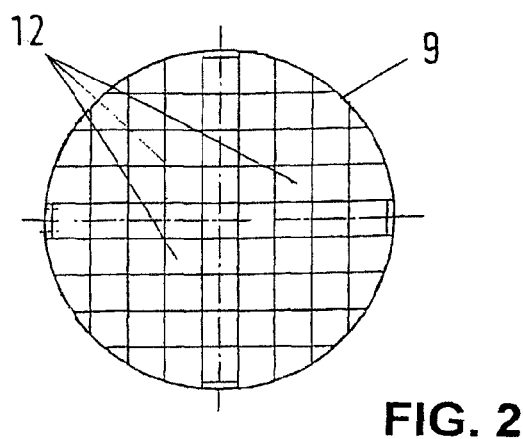
FIG. 2 a top view of a tray made up of cuboid cells
Figure 7:
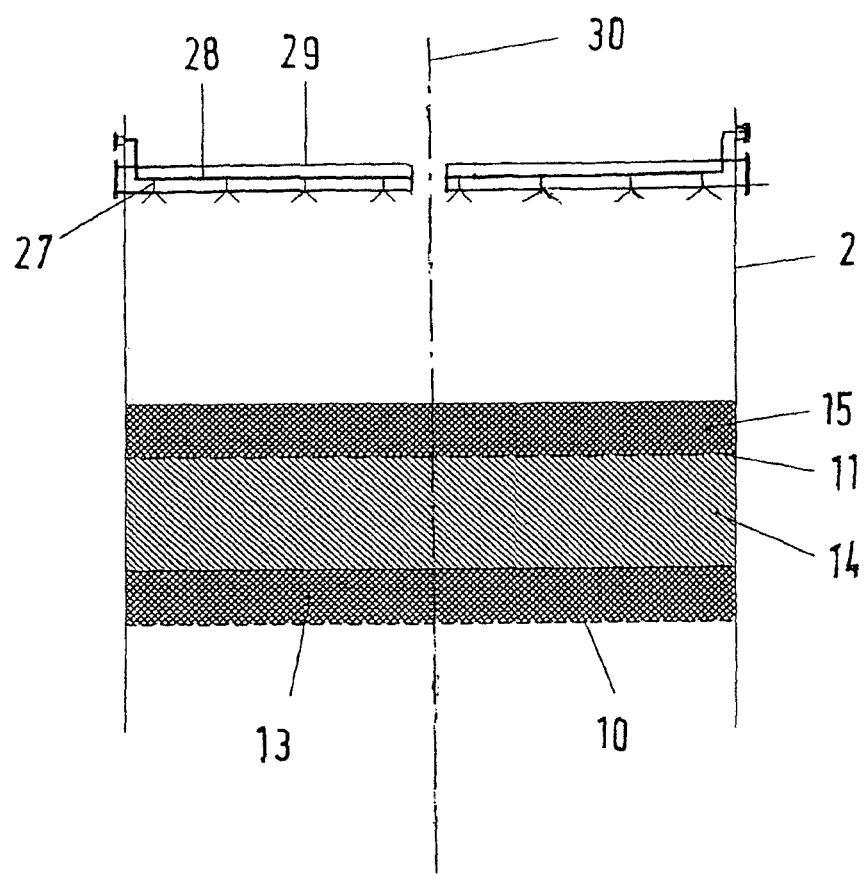

In accordance with FIG. 1 the reactor (1) is composed of a vertical, cylindrical, enclosed vessel (2) with six reactor stages arranged one below the other (3, 4, 5, 6, 7, 8) which, as shown in detail in FIG. 2 to FIG. 5 and the section (X) of FIG. 1 depicted in FIG. 7, an unsupported tray (9) made up of cuboid cells (12) covered with wire mesh (10, 11) on the bottom and top faces, firmly interconnected without interspaces. The lower section of the cells (12) is filled with a 100 mm thick layer (13) of ceramic balls whose diameter is 0.5" in the lower layer half and 0.25" in the upper layer half. A layer (14) made up of granular, shape-selective zeolite catalyst of the Pentasil type is packed on top of this layer of balls (13).

Figure 3:
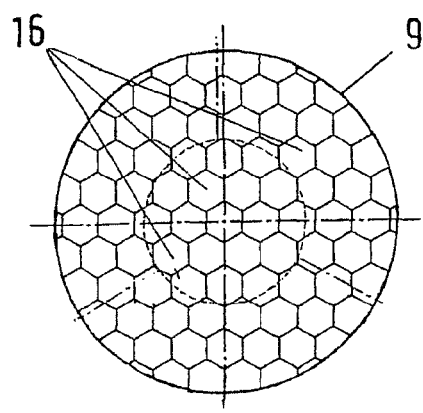
FIG. 3 a top view of a tray made up of honeycomb cells

The wire mesh (11) arranged on the top face is covered with a 100±10 mm thick layer (15) of ceramic balls having a diameter of 0.25". Starting from the vessel top, the thickness of the catalyst layer (14) is increasing steadily downstream from reaction stage to reaction stage (3, 4, 5, 6, 7, 8). In the first downstream reaction stage (3) the layer thickness is 253±10 mm, in the second reaction stage (4) it is 286±10 mm, in the third (5) it is 327±10 mm, in the fourth reaction stage (6) it is 384±10 mm, in the fifth reaction stage (7) it is 462±10 mm and in the sixth reaction stage (8) it is 588±10 mm. FIG. 3 shows a tray (9) made up of honeycomb cells (16). The layer thicknesses are variable.

In the interspaces (17, 18, 19, 20, 21) delimited by the reaction stages (3, 4, 5, 6, 7, 8), in each case an assembly of nozzle tubes (22, 23, 24, 25, 26) carrying twin-fluid nozzles (27) with external mixing effect incorporated at regular intervals and solid-cone characteristics at a jet angle of 30° is laid at regular spacing. The twin-fluid nozzles (27) atomize the liquid phase entering through tube (28), containing DME and MeOH and mainly consisting of water, having a temperature of 93° C., under the impact of the gas phase entering through tube (29) which is water-saturated and contains DME and MeOH at an average temperature of 175° C. The twin-fluid nozzles (27) ensure uniform spraying of the liquid phase in the form of aerosols. The large specific surface areas of the liquid phase produced by atomizing make for quick heat exchange and mass transfer between the aerosols on the one hand and the reaction mixture leaving the reaction stages (3, 4, 5, 6, 7) on the other.

Figure 4:
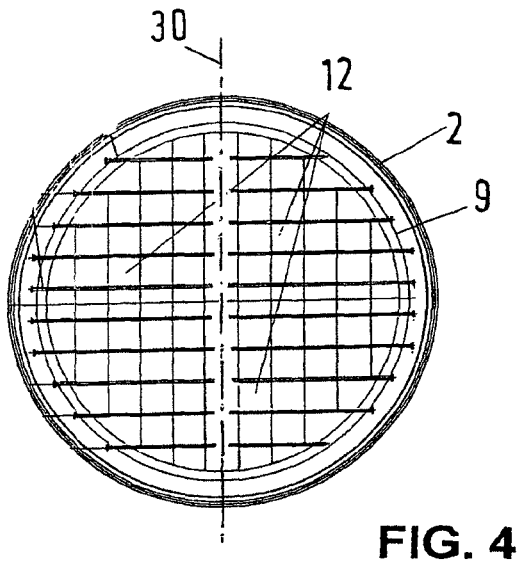
FIG. 4 a top view of a tray installed in a vessel and made up of cuboid cells with nozzle tubes arranged above it FIG. 5 a top view of the tray as shown in FIG. 4 with the base areas of the spray cones formed by the incorporated twin-fluid nozzles FIG. 6 a top view of the assembly of atomizers arranged in the form of involutes with the base areas of the spray cones produced by the incorporated twin-fluid nozzles FIG. 7 a magnified section (X) of FIG. 1

As shown in FIG. 4, the atomizer system installed in the interspace (17, 18, 19, 20, 21) delimited by two adjacent reaction stages (3, 4, 5, 6, 7, 8) is composed of mirror-image arranged nozzle tubes (22, 23, 24, 25, 26) closed at the ends pointing in the direction of flow and introduced horizontally from the periphery of the vessel (1) on both sides of a vertical plane (30) enclosing the vessel axis and laid parallel to each other at regular spacing in each case enclosing the vessel axis perpendicularly to the vertical plane (30) enclosing the vessel axis. The individual nozzle tubes (22, 23, 24, 25, 26) are arranged at the same straight-line distance from the walls of the cells (12) laid in the vertical planes enclosing the cell walls.

Figure 5:
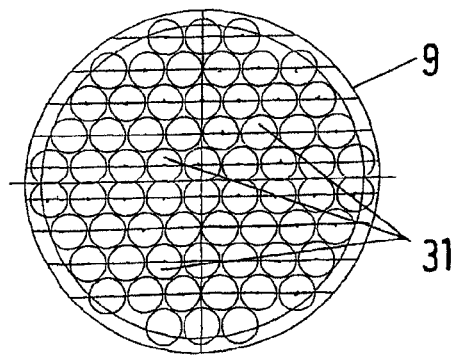

FIG. 5 shows the base areas (31) of the solid cones produced by the twin-fluid nozzles of the nozzle tubes (22, 23, 24, 25, 26).

Figure 6:
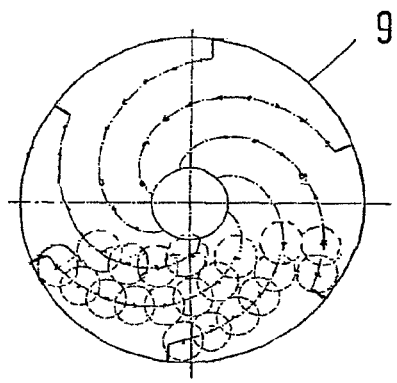

For special applications, it is possible to lay the nozzle tubes in the form of involutes as depicted in FIG. 6.

For operating the reactor the top of the vessel (2) is fed through line (32) with a gaseous material flow of 104199 kg/h at a temperature of 469° C. mainly consisting of 1819 kg MeOH, 3721 kg DME, 41841 kg water and 56753 kg hydrocarbons. From the vessel bottom (2), a gaseous material flow of 155405 kg/h having a temperature of 480° C. and mainly consisting of 443 kg MeOH, 217 kg DME, 72450 kg water and 79879 kg hydrocarbons is discharged through line (33).

Via line (34) a feed stream of 51207 kg/h, containing 9724 kg MeOH, 29266 kg DME and 12200 kg water and having a temperature of 156° C. is routed into a condensation vessel (35). After cooling to a mean temperature 150° C., the feed stream is supplied through line (36) to a two-phase separator (37) where it is split into a gas-phase stream of 44832 kg/h, in detail composed of 8497 kg MeOH, 29229 kg DME and 7089 kg water and a liquid-phase stream of 6375 kg/h, composed of 1227 kg MeOH, 38 kg DME and 5110 kg water. The gas-phase stream discharged through line (38) is split into five partial streams which in each case flow through one of the lines (39, 40, 41, 42, 43) into plate-type heat exchangers (44)

where they are heated to a temperature of 176° C. The liquid-phase stream leaving the two phase separator (37) through line (45) is cooled to a temperature of 93° C. in a heat exchanger (46), discharged through line (47) and split into five partial streams. From the gas phase partial streams discharged from the plate-type heat exchangers (44) via lines (48, 49, 50, 51, 52), one gas phase partial stream each and, from the liquid phase partial streams discharged via lines (53, 54, 55, 56, 57), one liquid phase partial stream each are fed to a nozzle tube (22, 23, 24, 25, 26) each and the liquid phase is uniformly atomized in the form of aerosols under the impact of the gas phase in the direction of the next following downstream reaction stage (4, 5, 6, 7, 8). By means of an additional heat exchanger (which is not shown) directly connected downstream of heat exchanger (46), the temperature of the liquid-phase stream can be lowered to 25° C.

In detail, the liquid phase partial stream of 800 kg/h supplied through line (57), mainly containing 171 kg MeOH, 5 kg DME, 713 kg $H_2O$, and the gas phase partial stream of 6259 kg/h fed through line (52), mainly containing 1186 kg MeOH, 4080 kg DME and 990 kg $H_2O$, are routed to the nozzle tube (22) and sprayed into the interspace (17) existing between the first and second downstream reaction stages (3, 4). The liquid phase partial stream of 1019 kg/h fed through line (56) essentially composed of 196 kg MeOH, 6 kg DME and 817 kg $H_2O$, and the gas phase partial stream of 7167 kg/h supplied through line (51), essentially containing 1358 kg MeOH, 4673 kg DME and 1133 kg $H_2O$, are passed on to the nozzle tube (23) and the liquid phase is sprayed into the interspace (18) between the second and third reaction stages (4, 5). In the interspace (19) delimited by the third and fourth reaction stages (5, 6), the liquid phase partial stream of 1197 kg/h, supplied through line (55) and essentially containing 230 kg MeOH, 7 kg DME and 959 kg $H_2O$, is atomized by the gas phase partial stream of 8417 kg/h supplied through line (50) and essentially containing 1595 kg MeOH, 5488 kg DME and 1331 kg $H_2O$. The liquid phase partial stream of 1,438 kg/h fed to the nozzle tube (25) through line (54) and essentially containing 277 kg MeOH, 9 kg DME and 1153 kg $H_2O$, is atomized by means of the gas phase partial stream of 10111 kg/h fed to the nozzle tube (26) through line (49), essentially composed of 1926 kg MeOH, 6592 kg DME and 1599 kg $H_2O$, into the interspace (20) delimited by the fourth and fifth reaction stages (6, 7). In the interspace (21) formed by the fifth and sixth reaction stages (7, 8), the liquid phase partial stream of 1831 kg/h supplied to the nozzle tube (26) through line (53) and essentially containing 351 kg MeOH, 11 kg DME and 1468 kg $H_2O$, is atomized by means of the gas phase partial stream of 12879 kg/h fed to the atomizer (27) via line (48), essentially containing 2441 kg MeOH, 8397 kg DME and 2037 kg $H_2O$.

The twin-fluid nozzles employed are designed for external mixing which means that the gas and liquid phase partial streams enter separately in each case and meet directly at the nozzle outlet. In this process, the gas phase contacts the solid jet emerging from the liquid gas mouthpiece outside the nozzle, atomizing it into a spectrum of fine droplets. An adjustment of the gas phase partial stream has virtually no influence on the volumes of the liquid phase partial streams. This applies analogously to the effect of a variation in liquid phase volume partial streams on the gas phase partial streams.

What we claim is:

1. A reactor for producing $C_2$- to $C_8$-olefins from gaseous oxygenate, and H2O and a material flow containing one or more of the hydrocarbons C2-, C4-, C5-, C6-, C7-, C8-olefins and -paraffins, having a temperature of 400 to 470° C., with several reaction stages, arranged within an enclosed, vertical vessel through which the material flow flows from top to bottom, in each case composed of a tray with a fixed-bed zone formed by a layer of granular molecular-sieve catalyst arranged on top of it, wherein the thickness of the layer of the molecular-sieve catalyst arranged in the cells is 100 to 1000 mm and increases steadily downstream from one reaction stage to the next following, wherein each tray is built up from cells, arranged side by side without interspace and firmly connected with each other and freely suspended inside the vessel, the cells being filled with a layer of molecular-sieve catalyst, an atomizer system in the interspace delimited upwards and downwards by two adjacent reaction stages and formed by an assembly of nozzle tubes for the uniform atomization of a liquid phase containing DME and/or MeOH, mainly consisting of $H_2O$ and having a temperature of between 25 and 150° C., through a water-saturated gas phase comprising DME and/or MeOH and having a temperature of 170 to 300° C., in the direction of the next following downstream reaction stage.

2. The reactor according to claim 1, wherein the molecular-sieve catalyst is a synthetic zeolite.

3. The reactor according to claim 1, wherein the particles of the molecular-sieve catalyst are of a cylindrical shape and have an average length of 3.5 to 7.0 mm and have a mean diameter of 3.1 to 3.4 mm.

4. The reactor according to claim 1 wherein the thickness of the layer of the molecular-sieve catalyst contained in the cells is 100 to 500 mm in the first reaction stage and 500 to 1000 mm in the last downstream reaction stage.

5. The reactor according to claim 1, wherein the cells forming the tray have the shape of a cuboid, cube or a straight equilateral prism.

6. The reactor according to claim 1, wherein the tray comprises a cover at both the bottom and top faces.

7. The reactor according to claim 1, wherein a 50 to 400 mm thick layer of inert balls, having diameter of 10 to 15 mm in the lower layer section and 5 to 8 mm in the upper section is arranged in the cells of the tray on top of the layer of molecular-sieve catalyst.

8. The reactor according to claim 6, wherein the cover on the top face of the tray comprises a 50 to 200 mm thick layer of inert balls having a diameter of 5 to 15 mm.

9. The reactor according to claim 5, wherein the nozzle tubes are provided with twin-fluid nozzles with external mixing effect arranged at regular intervals.

10. The reactor according to claim 1, wherein the atomizer system is composed of mirror-image arranged nozzle tubes closed at the ends pointing in the direction of flow and introduced from the periphery of the vessel on both sides of a vertical plane enclosing the vessel axis and laid at regular spacing in each case perpendicularly to the vertical plane enclosing the vessel axis, with the distance of the nozzle tube ends from the vertical plane enclosing the vessel axis being 20 to 500 mm.

11. The reactor according to claim 9, wherein, when the cells forming the tray have the shape of cubes or cuboids, the individual nozzle tube has in each case the same straight-line distance from the cell walls and is arranged in the vertical plane enclosing the cell walls.

12. The reactor according to claim 9, wherein the nozzle tubes provided as an assembly each are arranged in the form of involutes.

13. A process of operating the reactor for producing $C_2$- to $C_8$-olefins from gaseous oxygenate, and H2O and a material flow containing one or more of the hydrocarbons $C_2$-, $C_4$-, $C_5$-, $C_6$-, $C_7$-, $C_8$-olefins and -paraffins and having a temperature of 400 to 470° C., with several reactor stages arranged within an enclosed vertical vessel through which the material flow flows from top to bottom, in each case composed of a tray with a fixed-bed zone arranged on it, comprising a layer of granular molecular-sieve catalyst where each tray is built up from firmly interconnected cells arranged side by side without interspace and freely suspended inside the vessel, those cells being filled with a layer of molecular-sieve catalyst, an atomizer system in the form an assembly of nozzle tubes is installed in the direction of the respectively next following downstream reaction stage, in the interspace delimited in each case above and below by two adjacent reactor stages, for uniform atomization of a liquid phase comprising $H_2O$ and having a temperature of 50 to 150° C. through a water-saturated gas phase comprising DME and/or MeOH and having a temperature of 170 to 300° C., wherein a gaseous oxygenate, as well as a feed stream containing H2O and having a temperature of 150 to 300° C. are cooled to a temperature of 100 to 150° C. and split into a liquid phase and a gas phase, the gas and liquid phases being separated into several partial streams the number of which corresponds in each case to the number of interspaces existing between the reaction stages, the individual gas phase partial stream being fed to a nozzle tube in each case with a liquid phase partial stream, with the liquid phase being sprayed into the corresponding interspace by means of the gas phase.

14. The process in accordance with claim 13, wherein the liquid phase is atomized by means of the gas phase into a spectrum of fine droplets with a diameter of 10 to 100 μm.

15. The reactor according to claim 2 wherein the synthetic zeolite is selected from the group consisting of ZSM-5, Pentasil, MFI-Z or MeAPSO.

16. The reactor according to claim 3 wherein the particles of the molecular sieve catalyst have an average length of 2.1 to 4.5 mm.

17. The reactor according to claim 3 wherein the particles of the molecular sieve catalyst have an average diameter of 3.3 to 3.7 mm.

18. The reactor according to claim 6 wherein the cover is made of wire mesh, expanded metal or perforated plate.

19. The reactor according to claim 9 wherein the twin-fluid nozzles are designed with solid-cone characteristic and a jet angle of 15 to 35°.

\* \* \* \* \*